United States Patent [19]

Narang et al.

[11] 4,059,592
[45] Nov. 22, 1977

[54] ARYLSULFONYL TETRAZOLES

[75] Inventors: Saran A. Narang; Jacek Stawinski, both of Ottawa, Canada

[73] Assignee: Canadian Patents and Development Limited, Ottawa, Canada

[21] Appl. No.: 656,858

[22] Filed: Feb. 10, 1976

[51] Int. Cl.² .................................... C07D 257/04
[52] U.S. Cl. ............................................ 260/308 D
[58] Field of Search ................................ 260/308 D

[56] References Cited

U.S. PATENT DOCUMENTS

| 3,790,377 | 2/1974 | Smets et al. | 260/308 D |
| 3,941,804 | 3/1976 | Ilvespää et al. | 260/308 D |

Primary Examiner—Frederick E. Waddell
Attorney, Agent, or Firm—Alan A. Thomson

[57] ABSTRACT

Arylsulfonyl tetrazoles of the formula

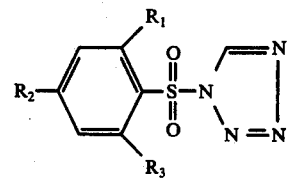

where $R_1$, $R_2$ and $R_3$ are selected from hydrogen, lower alkyl and lower alkoxy groups, and their preparation are described.

These compounds have been found to be advantageous condensing or coupling agents via phosphoester formation in polynucleotide synthesis.

6 Claims, No Drawings

ARYLSULFONYL TETRAZOLES

FIELD OF THE INVENTION

This invention is directed to novel arylsulfonyl tetrazole compounds, their method of preparation, and their use as improved coupling agents in polynucleotide synthesis.

DESCRIPTION OF THE PRIOR ART

5-Arylthioalkyl-tetrazoles have been prepared by reaction of the arylthioalkyl nitrile with an azide compound, and 5-arylsulfonylalkyl-tetrazoles prepared by further reaction with an oxidizing agent (see U.S. Pat. No. 3,337,576 Buchanan et al). 5-Para-nitrobenzene-sulfonamido-tetrazoles have been prepared by reacting 5-amino-tetrazole monohydrate with para-nitrobenzene sulfonyl chloride (see U.S. Pat. No. 2,209,243 Winnek). Both of these types of 5-tetrazole derivatives had biological activity.

Certain arylsulfonyl-1,2,4-triazoles were prepared from arylsulfonyl chloride and 1,2,4-triazole, and were found to have biological activity (see U.S. Pat. No. 3,293,259 Wolf).

No references have been noted to arysuflonyl tetrazoles nor their utility as coupling agents.

In polynucleotide synthesis the coupling of nucleotides is carried out by condensing the free phosphate group of one nucleotide to the free hydroxyl group of a second nucleotide or nucleoside, and such couplings can be repeated many times.

The development of dicyclohexylcarbodiimide (DCC), mesitylenesulfonyl chloride (MS) and triisopropylbenzenesulfonyl chloride (TPS) as reasonably effective condensing or coupling reagents has played a significant role in the synthesis of polynucleotides by the diester method (see S. A. Narang, K. Itakura, C. P. Bahl and N. Katagiri — J. Am. Chem. Soc. Vol. 96, page 7074, 1974). In the case of the triester synthetic approach (see K. Itakura, N. Katagiri, C. P. Bahl, R. H. Wightman and S. A. Narang — J. Am. Chem. Soc. Vol. 97, page 7327, 1975), triisopropylbenzenesulfonyl chloride (TPS) has been used almost exclusively as the condensing reagent because dicyclohexylcarbodiimide (DCC) will not activate phosphodiester functions and mesitylenesulfonyl chloride (MS) causes extensive sulfonation of the primary 5'-hydroxyl group of the nucleotide component thus blocking possible condensation.

The search for new condensing reagents was initiated because of our continued realization of low yields (ca. 20%) when attempting condensation with TPS of products containing purine bases, especially guanine. These low yields might be attributed to the liberation of hydrogen chloride from the triisopropylbenzenesulfonyl chloride (TPS) during the condensation reaction.

SUMMARY OF THE INVENTION

Arylsulfonyl tetrazoles have been prepared of the general formula

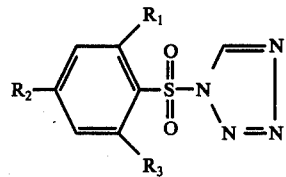

where $R_1$, $R_2$ and $R_3$ are selected from hydrogen, lower alkyl, and lower alkoxy groups, and these compounds have been found to be advantageous coupling agents. These 1-arylsulfonyl-tetrazoles can preferably have as aryl groups, unsubstituted phenyl or mono- or di-substituted-phenyl, or 2,4,6-trisubstituted-phenyl groups. The substituents can most suitably be lower alkyl or lower alkoxy groups having from 1 to 4 carbon atoms. Suitable aryl groups include phenyl, para-tolyl, para-ethylphenyl, paralower alkoxyphenyl (e.g. anisyl), mesityl, and 2,4,6-triisopropylphenyl. The phenyl compound tends to be more reactive and less stable than the substituted-phenyl compounds.

These arylsulfonyl tetrazoles can be prepared by reacting, in a non-polar organic solvent, an arylsulfonyl chloride with tetrazole, in the presence of a basic amine catalyst. Suitable solvents include dioxane, chloroform, carbon tetrachloride and benzene. Suitable basic amine catalysts include triethylamine, aniline and lutidine. Approximately equimolar amounts of the two reactants will normally be used. After the reaction is complete a precipitate will usually be present in the cooled reaction medium, and this precipitate should be removed and the liquor processed to recover the soluble arysulfonyl tetrazole.

In polynucleotide synthesis, an appropriate N-protected nucleotide or oligonucleotide phosphate and an appropriate N-protected nucleotide or oligonucleotide containing a free 5'-hydroxyl group are mixed in an appropriate aprotic organic solvent medium and treated with the arysulfonic tetrazole coupling agent. From about 2 to about 3 molar equivalents of coupling agent based on the 5'-protected component are suitable. The coupling or condensing reaction will normally take about 1-2 hours at room temperature. The reaction mixture is then inactivated and processed to recover the phosphoester product.

DESCRIPTION OF PREFERRED EMBODIMENTS

The following Examples illustrate the various aspects of the invention, and are not to be construed in a limiting sense. Alternative components and conditions will be apparent to those skilled in the art.

EXAMPLE 1

Preparation of Arylsulfonyltetrazoles

To a solution of dioxane (2 ml) containing triethylamine (10.1 mmoles) was added the appropriate arysulfonyl chloride (10 mmoles) and tetrazole (10 mmoles) with cooling. After 2 hours, the precipitate was filtered off, discarded, and the liquor evaporated to dryness. The solid residue was dissolved in chloroform (~50 ml) and washed with water (2 × 20 ml). The chloroform solution was dried over anhydrous sodium sulfate and after evaporation of solvent, the residue was recrystallized from an appropriate organic solvent as stated below. The isolated yield was 70-80%. Each of the compounds was characterized by its melting point, elemental analysis and NMR spectra as detailed below.

1-(Benzenesulfonyl) -tetrazole (BS-tetr.): White crystals m.p. 86-92° (Recrystallized from benzene) Elem Anal. Calcd. for $C_7H_6N_4O_2S$: C, 36.36; H, 3.05; N, 28.27. Found: C, 36.50; H, 3.00; N, 28.24. NMR (CDCL$_3$, ppm from trimethyl silicane TMS) 9.25 (1H, S, C$\underline{H}$ in tetrazole); 8.0 (5H, m. aromatic ring).

1-(Mesitylenesulfonyl)-tetrazole (MS-tetr.): White crystals m.p. 108-119° (Recrystallized from benzene) Elem. Anal. Calcd. $C_{10}H_{12}N_4O_2S$: C, 47.61; H, 4.79; N, 22.21. Found: C, 47.69; H, 4.84; N, 22.30. NMR (CDCL$_3$ ppm from TMS) 9.21 (1H, S, C$\underline{H}$ in tetrazole), 7.5 (2H, S, aromatic ring); 2.7 (6H, S, CH$_3$) ortho, 2.36 (3H, S, CH$_3$ para).

1-(2,4,6-Triisopropylbenzenesulfonyl)-Tetrazole (TPS-tetr.): White crystals m.p. 95°-97° (Recrystallized from benzenepetroleum ether), Elem. Anal. Calcd. $C_{16}H_{24}N_4O_2S$: C, 57.12; H, 7.19; N, 16.65. Found: C, 57.25; H, 7.20; N, 16.69. NMR (CDCL$_3$, ppm from TMS) 9.28 (1H, S, C$\underline{H}$ in tetrazole); 7.4 (2H, S, aromatic ring); 4.15 (2H, M, C$\underline{H}$ in ortho); 3.14 (1H, M, C$\underline{H}$ in para); 1.28 (18H, pseudoquartet, CH$_3$).

EXAMPLE 2

Synthesis of Polynucleotides of Defined Sequences

A 5'-O-dimethoxytrityl-N-protected oligonucleotide-3'-p-chlorophenyl phosphate (1 molar equiv.) and an appropriate N-protected oligonucleotide containing free 5'-hydroxyl (1.2 molar equiv.) were mixed in anhydrous pyridine (5ml per g) and treated with arylsulfonyl tetrazole (3 molar equiv. based on 5'-protected component) at room temperature. When the reaction was over (after 1-2 hours) as checked by tlc on silica-gel, the reaction mixture was decomposed with water (10 ml per g) with cooling followed by extraction with chloroform (100 ml per g). The chloroform layer was washed with 0.1 M triethylammonium bicarbonate (50 ml × 3) followed by water, dried over anhydrous sodium sulfate and evaporated to a gum in the presence of excess of toluene under reduced pressure. The gum was dissolved in choroform and purified by silica-gel column chromatography. The column was monitored by checking an aliquot from every second fraction collector tube on silica-gel tlc plate using chloroform-methanol (1-10% v/v) as eluent.

The following Table 1 gives comparisons of the yields of various di- and trinucleotide products using triisopropylbenzenesulfonyl chloride (TPS), a prior art coupling agent, and two arylsufonyl tetrazole coupling agents according to the invention. The reaction time was 0.5 hour in each case. The yields are seen to be significantly improved using the coupling agents of the invention. For the di- or trinucleotides as in Table 1, a reaction time of 0.5 hour was sufficient, but for higher polynucleotides a longer reaction time will normally be required.

TABLE 1

| 5'-Protected component (1 molar equiv.) | 3'-Protected component (1.2 molar equiv.) | Product | % Yield (using 2 molar equiv.) based on 5'-protected component | | |
|---|---|---|---|---|---|
| | | | TPS | MS-tetr. | TPS-tetr. |
| *Fully protected dinucleotides* | | | | | |
| [(MeO)$_2$Tr]dbzA-ClPh | dbzA$\tau$CE | [(MeO)$_2$Tr]dbzA$\tau$bzA$\tau$CE | 30 | 75 | 78 |
| [(MeO)$_2$Tr]T-ClPh | dacG$\tau$CE | [(MeO)$_2$Tr]dT$\tau$acG$\tau$CE | 34 | 65 | 68 |
| [(MeO)$_2$Tr]dacG-ClPh | dbzA$\tau$CE | [(MeO)$_2$Tr]dacG$\tau$bzA$\tau$CE | 22 | 66 | 52 |
| [(MeO)$_2$Tr]dbzC-ClPh | dacG$\tau$CE | [(MeO)$_2$Tr]dbzC$\tau$acG$\tau$CE | 38 | 70 | 80 |
| [(MeO)$_2$Tr]dbzA-ClPh | dT$\tau$CE | [(MeO)$_2$Tr]dbzA$\tau$T$\tau$CE | 52 | 73 | 81 |
| [(MeO)$_2$Tr]dbzA-ClPh | dbzC$\tau$CE | [(MeO)$_2$Tr]dbzA$\tau$bzC$\tau$CE | 68 | 74 | 70 |
| [(MeO)$_2$Tr]T-ClPh | dbzA$\tau$CE | [(MeO)$_2$Tr]dT$\tau$bzA$\tau$CE | 62 | 72 | 78 |
| [(MeO)$_2$Tr]dbzC-ClPh | dbzC$\tau$CE | [(MeO)$_2$Tr]dbzC$\tau$bzC$\tau$CE | 71 | 83 | 80 |
| [(MeO)$_2$Tr]dbzC-ClPh | T$\tau$CE | [(MeO)$_2$Tr]dbzC$\tau$T$\tau$CE | 68 | 79 | 82 |
| *Fully protected trinucleotides* | | | | | |
| [(MeO)$_2$Tr]dbzA$\tau$bzA-ClPh | T$\tau$CE | [(MeO)$_2$Tr]dbzA$\tau$bzA$\tau$T$\tau$CE | 45 | 74 | 71 |
| [(MeO)$_2$Tr]dbzA$\tau$T-ClPh | dbzA$\tau$CE | [(MeO)$_2$Tr]dbzA$\tau$T$\tau$bzA$\tau$CE | 51 | 76 | 78 |
| [(MeO)$_2$Tr]dbzA$\tau$T-ClPh | T(oAc) | [(MeO)$_2$Tr]dbzA$\tau$T$\tau$T(oAc) | 59 | 82 | 78 |
| [(MeO)$_2$Tr]dbzA$\tau$bzC-ClPh | dbzA$\tau$CE | [(MeO)$_2$Tr]dbzA$\tau$bzC$\tau$bzA$\tau$CE | 52 | 70 | 72 |
| [(MeO)$_2$Tr]dT$\tau$acG-ClPh | T$\tau$CE | [(MeO)$_2$Tr]dT$\tau$acG$\tau$T$\tau$CE | 32 | 64 | 52 |
| [(MeO)$_2$Tr]T$\tau$bzA-ClPh | T$\tau$CE | [(MeO)$_2$Tr]dT$\tau$bzA$\tau$T$\tau$CE | 55 | 72 | 70 |
| [(MeO)$_2$Tr]dacG$\tau$bzA-ClPh | dacG$\tau$CE | [(MeO)$_2$Tr]dacG$\tau$bzA$\tau$acG$\tau$CE | 18 | 58 | 40 |
| [(MeO)$_2$Tr]dbzC-ClPh | dacG$\tau$acG(oAc) | [(MeO)$_2$Tr]dbzC$\tau$acG$\tau$acG(oAc) | 20 | 68 | 59 |
| [(MeO)$_2$Tr]dbzC$\tau$bzC-ClPh | dacG$\tau$CE | [(MeO)$_2$Tr]dbzC$\tau$bzC$\tau$acG$\tau$CE | 32 | 61 | 58 |
| [(MeO)$_2$Tr]dbzC$\tau$T-ClPh | dbzC$\tau$CE | [(MeO)$_2$Tr]dbzC$\tau$T$\tau$bzC$\tau$CE | 65 | 76 | 80 |

We claim:
1. An arylsulfonyl tetrazole of the formula

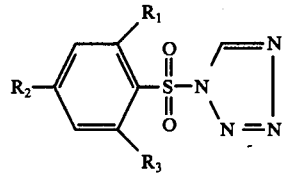

where R$_1$, R$_2$ and R$_3$ are selected from hydrogen, lower alkyl and lower alkoxy groups, the alkyl and alkoxy groups having from 1 to 4 carbon atoms.

2. The tetrazole compound of claim 1 wherein the R groups are methyl, methoxy or triisopropyl.

3. The tetrazole compound of claim 1 wherein the R$_2$ group is methyl or methoxy, and R$_1$ and R$_3$ are hydrogen, methyl or methoxy.

4. The tetrazole compound of claim 1 being the 1-(benzenesulfonyl)-tetrazole.

5. The tetrazole compound of claim 1 being the 1-(mesitylenesulfonyl)-tetrazole.

6. The tetrazole compound of claim 1 being the 1-(triisopropylbenzenesulfonyl)-tetrazole.

* * * * *